(12) United States Patent
Knudsen

(10) Patent No.: US 9,192,637 B1
(45) Date of Patent: Nov. 24, 2015

(54) MILKWEED SEED OIL ADMINISTERED TO ANIMALS

(71) Applicant: Natural Fibers Corporation, Ogallala, NE (US)

(72) Inventor: Herbert D. Knudsen, Ogallala, NE (US)

(73) Assignee: NATURAL FIBERS CORPORATION, Ogallala, NE (US)

( * ) Notice: Subject to any disclaimer, the term of this patent is extended or adjusted under 35 U.S.C. 154(b) by 0 days.

(21) Appl. No.: 13/624,327

(22) Filed: Sep. 21, 2012

Related U.S. Application Data

(60) Provisional application No. 61/538,467, filed on Sep. 23, 2011.

(51) Int. Cl.
*A61K 36/27* (2006.01)
*A61K 36/185* (2006.01)

(52) U.S. Cl.
CPC .................................... *A61K 36/27* (2013.01)

(58) Field of Classification Search
None
See application file for complete search history.

(56) References Cited

U.S. PATENT DOCUMENTS

| | | | | |
|---|---|---|---|---|
| 2,480,769 | A  * | 8/1949 | Reed | 554/9 |
| 7,351,403 | B2 * | 4/2008 | Harry-O'kuru | 424/59 |
| 2011/0135747 | A1* | 6/2011 | Polich | 424/539 |
| 2013/0109674 | A1* | 5/2013 | Leighton et al. | 514/217 |

* cited by examiner

*Primary Examiner* — Chris R Tate
*Assistant Examiner* — Randall Winston
(74) *Attorney, Agent, or Firm* — Curatolo Sidoti Co., LPA; Joseph G. Curatolo; Salvatore A. Sidoti

(57) ABSTRACT

Milkweed seed oil administered to an animal improves reduces the symptoms of headaches and improves the health of the animal. Administering an effective amount of milkweed seed oil to the area around the headache of animal results in an improvement in the symptoms of headaches as compared to the symptoms experienced by the animal both before and after the milkweed seed oil was administered.

23 Claims, No Drawings

MILKWEED SEED OIL ADMINISTERED TO ANIMALS

CROSS REFERENCE TO RELATED APPLICATIONS

This application claims the benefit of the filing date under 35 U.S.C. 119(e) from U.S. Provisional Application For Patent Ser. No. 61/538,467, filed Sep. 23, 2011, which is hereby incorporated by reference.

TECHNICAL FIELD

A composition and method are provided for improving mammalian animal health. Provided is a treatment method to improve the health of an animal suffering from headaches by treating an animal with milkweed seed oil in addition to or in substitution of other conventional treatment methods.

BACKGROUND

The symptoms of headaches can be debilitating. In the United States, it is reported that over 100 million people suffer from headaches. There are over 150 different types of diagnostic headache categories. The list includes but is not limited to tension headaches, migraine headaches, mixed headaches of migraine and tension, sinus headaches, acute headaches, hormone headaches, chronic progressive headaches and many more types of headaches.

Migraine headaches are especially devastating to the person suffering the effects and pain. In the United States over 37 million people suffer from migraine headaches. Migraines usually have three stages: 1) Prodrome; 2) Attack; and 3) Postdrome. Women are about three times more likely to have migraine headaches as men. Migraine headaches are of special interest because people cannot participate in normal activities because of the pain of migraine headaches, especially during the Attack stage. Migraine headaches are a major cause of chronic disability in the country.

Proper treatment of headaches will depend on several factors including the type, severity and frequency of the headache and its cause. A high percentage of ordinary headaches do not require professional medical attention. A host of medications are on the market that will deal with these headaches. Unfortunately, many of these medications have negative side effects.

Milkweed seed oil treatments of headaches covered in this invention are effective in dealing with these headache symptoms as shown in the discussion and examples of this document. Milkweed seed oil treatments have also demonstrated positive side effects not negative side effects. The improvement in animal health can be monitored by the amount of pain experienced and the amount of mobility of which the animal is capable. Quick, effective and positive treatments of headaches without negative side effects are desired in the art.

SUMMARY

Provided is a method for reducing the symptoms of headaches in an animal comprising administering an effective amount of milkweed seed oil to the animal.

DETAILED DESCRIPTION

Milkweed seed oil is administered to mammalian animals to reduce or alleviate the symptoms of headaches and to improve the animal health. In certain embodiments, the milkweed seed oil functions as an anti-inflammatory. The improvement in health is determined by the reduction in pain, reduction in inflammation and/or the amount of medications used to control pain and/or inflammation. It is also measured by the increase in mobility of the animal. Milkweed seed oil formulations may be administered to mammalian animals for non-therapeutic or therapeutic applications.

Milkweed seed oil as disclosed herein is a product comprised primarily of fatty acids and including small quantities of additional ingredients. The milkweed seed oil is administered topically, orally, or internally to an animal in a sufficient amount and for a period of time sufficient to reduce or alleviate the symptoms, especially pain, of an animal having headaches and/or the ability of an animal having a headache to move about normally.

Milkweed seed oil is produced from the seeds found in the pods of milkweed plants, which are known under the Latin binomial name *Asclepias*. Any of the numerous *Asclepias* plants can be used as a source of seed for producing milkweed seed oil. The most prominent sources of milkweed seeds in the work on certain embodiments to date are seeds from *Asclepias Syriaca* and *Asclepias Speciosa*. Other non-limiting sources of milkweed seed oil may include, for example, *Asclepias albicans, Asclepias amplexicaulis, Asclepias californica, Asclepias cordifolia, Asclepias cryptocerus, Asclepias curassavica, Asclepias eriocarpa, Asclepias erosa, Asclepias exaltat, Asclepias fascicularis, Asclepias fascicularis, Asclepias fruticosa, Asclepias humistrata, Asclepias incarnata, Asclepias lanceolata, Asclepias linaria, Asclepias linearis, Asclepias meadii, Asclepias nyctaginifolia, Asclepias obovata, Asclepias physiocarpa, Asclepias purpurascens, Asclepias quadrifolia, Asclepias solanoana, Asclepias speciosa, Asclepias subulata, Asclepias sullivantii, Asclepias syriaca, Asclepias tuberose, Asclepias variegate, Asclepias verticallata, Asclepias vestita* and *Asclepias vincetoxicum*. This list of *Asclepias* species is not exhaustive as scientists believe that there may be over 800 different varieties of *Asclepias*.

Production of Milkweed Seed Oil. In certain embodiments, milkweed seed oil is produced by cold pressing substantially clean milkweed seeds in a seed press or by extracting the oil from the seed with a non-polar solvent to recover the milkweed seed oil. Suitable non-polar solvents include but are not limited to hexane, carbon dioxide and petroleum ether. Extraction with these solvents produces a liquid lipid product comprising primarily fatty acids, and in certain embodiments, a liquid lipid product of fatty acids.

Milkweed seed may also contain toxic cardenolides that can be recovered from the milkweed seed with a polar solvent as a powder or as a dissolved solid in the polar solvent. Non-polar solvents used in extracting the fatty acids from the seed may be selected so that the effectiveness of the milkweed seed oil is not impaired by the presence of cardenolides. Rogers E. Harry-Okuru and Thomas P. Abbott in Industrial Crops and Products 7 (1997) 53-58 concluded that "Cold-pressed and solvent (petroleum ether) extracted milkweed oils show no detectable cardenolides by the alkaline TNBP method at a limit of less than 1.0 ppm." In one embodiment, milkweed seed oil is produced that has no detectable cardenolides at a limit of less than 1 part per million.

Raw milkweed seed oil produced in pressing equipment or in extraction with a solvent may need to be filtered to remove fine particles of the milkweed seed. This can be accomplished with traditional seed oil separating equipment, efficient filtration systems or with other known means of separation.

A typical fatty acid profile of milkweed seed oil produced in a seed press is shown below in Table 1. As can be deduced from the data, the milkweed seed oil had a large majority of fatty acids commonly found in food grade vegetable oils. The oil also contained two less common fatty acids, C16:1 palmitoleic acid and C18:1 cis-vaccenic acid. The milkweed seed oil with the fatty acid profile in Table 1 was used in the experiments described below.

TABLE I

Milkweed Seed Oil Fatty Acid Profile

| >1% Concentration | |
|---|---|
| C16:0 Palmitic Acid | ~6.6% |
| C16:1 Palmitoleic Acid | ~11.8% |
| C17:0 Heptadecanoic Acid | ~2.4% |
| C18:1 n-9 Oleic Acid | ~23.9% |
| C18:1 n-7 cis-Vaccenic acid | ~12.4% |
| C18:2 Linoleic Acid | ~40.4% |
| C18:3 Linolenic Acid | ~1.3% |

In addition to the fatty acids shown in the table above, a minor amount of other fatty acids which are present at concentrations below 1% of the oil were in the milkweed seed oil recovered. Those fatty acids include the following:

TABLE II

Milkweed Seed Oil Fatty Acid Profile

| <1% Concentration | |
|---|---|
| C17:1 10-Heptadecanoic Acid | ~0.2 |
| C18:0 Stearic Acid | ~0.2 |
| C20:0 Arachidic Acid | ~0.5 |
| C20:1 Eicosenoic Acid | ~0.2 |
| C22:2 Docosadienoic Acid | ~0.4 |
| C23:0 Tricosanoic Acid | ~0.4 |
| C24:0 Lignoceric Acid | ~0.4 |
| C24:1 Nervonic Acid | ~0.2 |

Milkweed seed oil may also contain other components in lesser amounts. Other ingredients identified in the oil used in the experiment below include phospholipids (about 2.15 g/100 g), digitoxin like components (about 890 mg/100 g), stigmasterol (about 272.8 mg/100 g), alpha-tocopherol (about 37.8 mg/100 g), β-sitosterol (about 23.7 mg/100 g), and campesterol (about 13.6 mg/100 g). In addition, vitamins, phytosterols, carotenes and other trace ingredients found in milkweed seed oil may have a positive impact on animal health even at very low concentrations.

Milkweed seed used to produce milkweed seed oil differs based on the genetic line of *Asclepias* used in production, the weather during the milkweed pod growth and the geographical region where the milkweed was grown. These variations, however, produce seed with oil contents within the limits of the current composition and method.

Also, milkweed seed oil may be produced not only from milkweed seed, but also from milkweed oil press cake. Press cake is the solid discharge from a seed press after some but not all of the oil is pressed out of the seed. The milkweed seed oil press cake can be rerun in a press to produce more milkweed seed oil or the press cake can be solvent extracted. Press cake extractions may provide unique, but similar fatty acid profiles to the data shown in Table 1. Milkweed seed oil from these sources are effective according to the present composition and method, provided that liquid fatty acid oil is recovered and that cardenolides are not present in the oil at a level that is harmful to the animal, in most embodiments such cardenolides being below about 1 part per million.

Factors Affecting the Application of Milkweed Seed Oil to Animals. A method is provided for improving the health of a mammalian animal and for reducing or alleviating the symptoms of headaches. The method comprises administering an effective amount of the disclosed milkweed seed oil formulation to an animal. Milkweed seed oil may be administered to animals topically, orally or internally. In certain embodiments, the amount administered daily measured as 100% milkweed seed oil is less than about 5 grams per kilogram of body weight, and in some embodiments is less than about 1 gram per kilogram of body weight. Lower amounts of milkweed seed oil, such as about 0.1 gram per kilogram of body weight and even about 0.01 gram per kilogram of body weight have been proven effective.

For topical applications, milkweed seed oil can be administered to any area of the skin adjacent to the headache. The milkweed seed oil penetrates through the skin quickly. The milkweed seed formulation may be incorporated into a wide variety product forms for topical administration to a subject. By way of illustration, but not of limitation, the milkweed seed oil may be incorporated into topical balms, creams, gels, lotions, ointments, salves, sprays (aerosol and non-aerosol sprays), rollerballs and dermal patches for topical administration of the milkweed seed oil formulation.

The milkweed seed oil liquid formulation administered to an animal may be milkweed seed oil alone or milkweed seed oil in combination with other ingredients that do not block the beneficial effect of milkweed seed oil. Formulated compositions of liquid milkweed seed oil and other components are included as embodiments of the present composition and method. The concentration of milkweed seed oil in the formulations of certain embodiments comprises about 50 weight % or more of milkweed seed oil, with formulations containing about 60 weight % or more of milkweed seed oil. Formulations containing about 40 weight % or more of milkweed seed oil also being useful embodiments.

Optional compatible ingredients in milkweed seed oil liquid formulations include at least one of food grade vegetable oils, nut oils, fish oils, fragrances and other seed oils. Jojoba oil may also be used effectively in combination with milkweed seed oil. Suitable vegetable oils include but are not limited to at least one of olive oil, canola oil, safflower oil, corn oil, soybean oil, sunflower seed oil, or flax oil. Suitable nut oils include but are not limited to at least one of walnut oil, almond oil, or macadamia nut oil. A wide range of fragrances are available commercially that may be used to alter the odor of the milkweed seed oil product formulation.

The dosage of the milkweed seed oil administered to an animal depends on the concentration of the milkweed seed oil in the formulation. In topical applications, excellent results have been obtained on about a 93 kilogram animal using a formulation comprising about 77% milkweed seed oil in a dose of about 0.3 gram per application 2 times per day in separated periods of time. An acceptable administration rate to the animal is a daily amount of about 0.006 grams per kilogram of body weight. This dosage is within an acceptable daily rate of administration—less than about 0.01 grams per kilogram of body weight. The same amount of milkweed seed oil could be administered using about one gram doses of a blend containing from about 20% to about 30% milkweed seed oil and from about 70% to about 80% vegetable or jojoba oil.

Evidence indicates that total daily use of less than about 20 grams of milkweed seed oil, calculated as 100% milkweed seed oil, is more than sufficient to produce the desired improvement in headache pain. The dosage of milkweed seed oil taken orally or internally rather than topically may vary from these general guidelines for topical applications. Experience has shown that the animal administered milkweed seed oil topically demonstrates the impact of the formulation on the body of the animal. Changes in the dosage may be necessary in response to these observations.

Suitable ranges of milkweed seed oil dosages are shown by the non-limiting experimental tests below. Higher dosages or longer usage of milkweed seed oil could further improve health managing pain and mobility. It may be necessary to continue milkweed seed oil treatment to maintain the improved pain relief results, but there is evidence that milkweed seed oil has a positive impact on headache pain for a few days after daily application or consumption terminates. The need to have an effective amount of milkweed seed oil may require the user to alter the dosage over time to provide the desired benefits as measured by the difference in the level of pain.

Oral administration of milkweed seed oil has also been found to be beneficial in relieving headache pain and increasing mobility of the animal affected by the headache.

Milkweed seed oil may be formulated into a wide variety of orally ingestible compositions. Liquid forms include solutions, suspensions, emulsions, gels, syrups, liquid-containing capsules, and the like. According to certain embodiments, the liquid milkweed seed oil formulation is contained within an orally ingestible capsule. Upon ingestion, the liquid-containing capsule is digested and the liquid milkweed seed oil formulation is released from the capsule.

According to certain illustrative embodiments, the milkweed seed oil may be formulated with an orally ingestible carrier such as an orally ingestible liquid carrier to provide an orally ingestible milkweed seed oil. For example, the milkweed seed oil may be formulated with an orally ingestible liquid carrier to provide a beverage. The beverages may be provided ready for oral ingestion or may be provided in a concentrate that requires dilution with acceptable liquids prior to oral ingestion. According to other embodiments, the milkweed seed oil may be formulated into other solid orally ingestible product forms or carriers, such as powders, pills, lozenges, tablets, caplets, capsules, gel capsules, edible films, and the like. Flavoring agents may also be added to the orally ingestible products to provide a more palatable orally ingestible composition.

The orally ingestible milkweed seed oil formulation may further include nutritionally effective amounts of an additional agent. According to certain embodiments, the milkweed seed oil formulation may further comprise effective amounts of at least one vitamin, or at least one mineral or a combination of at least one vitamin and at least one mineral. According to certain embodiments, the milkweed seed oil formulation comprises a nutritionally effective amount of milkweed seed oil and a nutritionally effective amount of at least one vitamin. According to certain embodiments, the milkweed seed oil formulation may comprise a nutritionally effective amount of milkweed seed oil and a nutritionally effective amount of at least one vitamin. According to certain embodiments, the milkweed seed oil may comprise a nutritionally effective amount of milkweed seed oil formulation and a nutritionally effective amount of at least one vitamin and at least one mineral. The milkweed seed oil formulation may also include at least one amino acid alone or at least one amino acid in combination with at least one vitamin and/or at least one mineral.

Experimental Production of Milkweed Seed Oil in a Seed Press. According to these experiments, clean milkweed seed from *Asclepias Syriaca* and *Asclepias Speciosa* plants was pressed in a screw press to produce raw milkweed seed oil. The raw oil was strained in two layers of high thread count cotton fabric at atmospheric pressure to produce clean milkweed seed oil. The clean milkweed seed oil was placed in a marked container, sealed and placed in a constant temperature room maintained at about 70 degrees Fahrenheit. Samples of milkweed seed oil for the experiments described below were taken from the stored oil and maintained in marked sealed bottles. The fatty acid profile of milkweed seed oil produced in this experiment is shown above in Table I and Table II.

Experimental Testing of Milkweed Seed Oil Properties. The milkweed seed oil produced above was tested by a certified, independent laboratory that specializes in natural oil analysis. A sample of milkweed seed oil from this production run was analyzed for antioxidant capacity. Oxygen Radical Absorbance Capacity (ORAC) tests conducted on milkweed seed oil tested for total antioxidant capacity showed results of 9,700 micromoles of Trolox equivalents per 100 grams. This rating is about 50% higher than the rating of blueberries.

Experimental Testing of Milkweed Seed Oil Administered to a 48 Year Old Female Suffering the Attack Stage of a Migraine Headache. A test to determine the impact of milkweed seed oil treatment was conducted on a 48 year old female human being who had been diagnosed by her medical doctor as having migraine headaches and from her statements has suffered migraine headaches for over 20 years. Natural Fibers Corporation supplied the woman a bottle of Milkweed Balm containing a liquid fatty acid oil blend of 65% milkweed seed oil, 32% crude soybean oil and 3% jojoba oil. In the Attack stage of a migraine headache, the woman rated her pain problem as major; a rating of 5 on a 1 to 5 scale where 1 was no pain and 5 was major pain. In the Attack stage, the woman topically applied 2 dropper drops (5% of a ml each) on her neck and one dropper drop (5% of a ml) to each temple. Within a few minutes after treatment with the milkweed seed oil blend, the woman felt her muscles relax and the pain subsided. The woman rated her pain after treatment as 0, on the scale of 1-5. The rating was interpreted as a 1, no pain. Her mobility was also restored.

Experimental Testing of Milkweed Balm Effectiveness on Headaches in Two Places of a 40 Year Old Woman. A 40 year old woman in good health suffered a headache simultaneously in two separate places on her head. She put one drop (5% of a ml) of the Milkweed Balm described above on the first area of pain and gently rubbed the oil throughout the area of pain. In the same manner, she rubbed one drop into the other area of pain. The pain in both areas of pain quickly went away.

Experimental Testing of Milkweed Balm Effectiveness on Sinus Headaches. A 32 year old woman in good health suffered a sinus headache in the two sinus cavities above the eyes. She put one drop (5% of a ml) of the Milkweed Balm described above on the end of her index finger. She rubbed the oiled first index finger and her second index finger together. Simultaneously, she gently applied Milkweed Balm over her eyes moving from the middle of the forehead to the outer edges of her eyes. Within 5 minutes after the application the sinus headache was gone, and she suffered no more pain.

Experimental Test of Milkweed Balm Effectiveness on Prodrome Migraine headaches. A 38 year old woman in good health but for a history of migraine headaches was tested. When she sensed the first stage of a migraine headache, Prodrome, she would begin consumption of a combination of drugs prescribed by her personal doctor. When she took these drugs she would normally wake up the morning after with a headache, not an Attack migraine headache, but a painful headache. In the first experiment, the woman took her combination of prescribed drugs and, in addition, applied one drop (5% of a ml) of the Milkweed Balm described above to the area of pain on her head. She was thrilled to wake up in the morning without any headache. Moreover, the Attack stage of her normal migraine headache cycle did not materialize. At a later date in a second experiment when she sensed the first stage of a migraine headache, Prodrome, she applied one drop of Milkweed Balm to the area of her head that hurt in this first stage of the migraine headache cycle. The warning signs of Prodrome disappeared quickly. To her delight the Attach stage of the migraine headache cycle did not follow. The woman was able to function normally during the entire time that she normally would have been disabled because of the migraine headache.

There are many possible treatments of animals with milkweed seed oil to alleviate pain from headaches according to the compositions and methods discussed and exemplified herein. Although the embodiments have been described in detail through the above description and the preceding examples, these examples are for the purpose of illustration only and it is understood that variations and modifications can be made by one skilled in the art to identify and administer these treatments using milkweed seed oil without departing from the spirit and the scope of the disclosure. It should be understood that the embodiments described above are not only in the alternative, but can be combined.

What is claimed is:

1. A method for reducing one or more symptoms of a migraine or sinus headache in an animal suffering therefrom comprising administering to the subject an effective amount of a composition comprising milkweed seed oil obtained from an *Asclepias* plant.

2. The method of claim 1, wherein the subject is a human being.

3. The method of claim 1, wherein the source of the milkweed seeds used for producing the milkweed seed oil comprises any one of the following plants: *Asclepias syriaca, Asclepias speciosa, Asclepias albicans, Asclepias amplexicaulis, Asclepias californica, Asclepias cordifolia, Asclepias cryptocerus, Asclepias curassavica, Asclepias eriocarpa, Asclepias erosa, Asclepias exaltat, Asclepias fascicularis, Asclepias fascicularis, Asclepias fruticosa, Asclepias humistrata, Asclepias incarnata, Asclepias lanceolata, Asclepias linaria, Asclepias linearis, Asclepias meadii, Asclepias nyctaginifolia, Asclepias obovata, Asclepias physiocarpa, Asclepias purpurascens, Asclepias quadrifolia, Asclepias solanoana, Asclepias speciosa, Asclepias subulata, Asclepias sullivantii, Asclepias syriaca, Asclepias tuberose, Asclepias variegate, Asclepias verticallata, Asclepias vestita, Asclepias vincetoxicum*, or mixtures thereof.

4. The method of claim 1, wherein the composition further comprises at least one of amino acids, food grade vegetable oils, nut oils, fragrances, vitamins, minerals, other seed oils, or mixtures thereof.

5. The method of claim 4, wherein the vegetable oils comprise at least one of olive oil, canola oil, safflower oil, corn oil, soybean oil, sunflower seed oil, flax oil, or mixtures thereof.

6. The method of claim 4, wherein the nut oils comprise at least one of walnut oil, almond oil, macadamia nut oil, or mixtures thereof.

7. The method of claim 1, wherein the composition further comprises jojoba oil.

8. The method of claim 1, wherein the composition further comprises jojoba oil and crude soybean oil.

9. The method of claim 1, wherein the composition is formulated into an orally ingestible product or a topically administered product.

10. The method of claim 9, wherein the composition comprises an orally ingestible product comprising a therapeutically effective amount of the milkweed seed oil.

11. The method of claim 10, wherein the orally ingestible product is in a liquid form or a solid form.

12. The method of claim 11, wherein the liquid form is selected from the group consisting of solutions, suspensions, emulsions, gels, syrups, liquid-containing capsules, and mixtures thereof.

13. The method of claim 11, wherein the solid form is selected from the group consisting from powders, pills, lozenges, tablets, caplets, capsules, gel capsules, edible films, and mixtures thereof.

14. The method of claim 10, wherein the orally ingestible product comprises a flavoring agent.

15. The method of claim 1, wherein the composition comprises a topically administered product comprising a therapeutically effective amount of the milkweed seed oil.

16. The method of claim 15, wherein the topically administered product comprises topical balms, creams, gels, lotions, ointments, salves, sprays, rollerballs and dermal patches.

17. The method of claim 16, wherein the spray comprises an aerosol spray or a non-aerosol spray.

18. The method of claim 1, wherein the amount of the milkweed seed oil administered to the subject per day is less than about 5 grams per kilogram of body weight.

19. The method of claim 1, wherein the amount of the milkweed seed oil administered to the subject per day is less than about 0.1 grams per kilogram of body weight.

20. The method of claim 1, wherein the amount of the milkweed seed oil administered to the subject per day is less than about 0.01 grams per kilogram of body weight.

21. The method of claim 1, wherein the symptom of the migraine or sinus headache is pain.

22. The method of claim 1, wherein the symptom of the migraine or sinus headache is a mobility problem.

23. The method of claim 1, wherein the symptom of the migraine or sinus headache is pain and a mobility problem.

* * * * *